United States Patent [19]

Lachiver et al.

[11] Patent Number: 4,736,295

[45] Date of Patent: Apr. 5, 1988

[54] METHOD AND APPARATUS FOR MATHEMATICAL CHARACTERIZATION OF THE ELECTROCARDIOGRAM

[76] Inventors: Gerard Lachiver, c.p. 361, North Hatley, Quebec, Canada, J0B 2C0; France Bessette, 195-204 Calixa Lavallée, Magog, Quebec, Canada, J1X 4X4; Wolf D. Seufert, R.R. 5, Sherbrooke, Quebec, Canada, J1H 5H3

[21] Appl. No.: 654,555

[22] Filed: Sep. 26, 1984

[51] Int. Cl.$^4$ .................. G06F 15/42; G06G 7/60
[52] U.S. Cl. ................................ 364/417; 364/169
[58] Field of Search ............ 364/417, 169, 478, 728, 364/512

[56] References Cited

U.S. PATENT DOCUMENTS

| | | |
|---|---|---|
| 3,442,264 | 5/1969 | Levitt . |
| 3,504,164 | 3/1970 | Farrell . |
| 3,609,319 | 9/1971 | Clifford, Jr. . |
| 3,634,661 | 1/1972 | Fitzner . |
| 3,858,034 | 12/1974 | Anderson . |
| 3,860,803 | 1/1975 | Levine .............................. 364/514 |
| 3,882,304 | 5/1975 | Walters . |
| 4,022,192 | 5/1977 | Laukien . |
| 4,090,505 | 5/1978 | Motara . |
| 4,115,864 | 9/1978 | Vick . |
| 4,124,894 | 11/1978 | Vick et al. . |
| 4,136,690 | 1/1979 | Anderson et al. . |
| 4,292,977 | 10/1981 | Krause . |
| 4,633,884 | 1/1987 | Imai et al. ............................ 364/415 |

OTHER PUBLICATIONS

B. Carnahan et al., "Interpolation and Approximation", in: Applied Numerical Methods, p. 63, (John Wiley & Sons, Inc., N.Y., 1969).
T. N. E. Greville, "Spline Functions, Interpolation, and Numerical Quadrature", from: Mathematical Methods for Digital Computers, vol. II, pp. 152-168, A. Ralston & H. S. Wilf, eds., (John Wiley & Sons, Inc., N.Y., 1967).

Primary Examiner—Clifford C. Shaw
Assistant Examiner—Lincoln Donovan
Attorney, Agent, or Firm—Cushman, Darby & Cushman

[57] ABSTRACT

Strategic points on an input waveform are selected and a continuous trace is then laid through the sequence of points by an interpolation method, known as the spline function, to reconstruct the original waveform with high fidelity. One application of the present apparatus is in the reconstruction of an electrocardiographic trace.

8 Claims, 5 Drawing Sheets

METHOD AND APPARATUS FOR MATHEMATICAL CHARACTERIZATION OF THE ELECTROCARDIOGRAM

FIELD OF THE INVENTION

The present invention pertains to an apparatus and method for the mathematical characterization of a waveform in order to obtain an accurate reconstruction of said waveform. More particularly, the present invention relates to an apparatus and method for the faithful reconstruction of an electrocardiographic trace.

BACKGROUND OF THE INVENTION

An electrocardiogram is a record of the electrical phenomena occurring in the heart to produce the coordinated contraction of the various chambers which assures an adequate circulation of blood through the body. The electrical fields thus generated follow the activity of the heart with time and are measured with electrodes at multiple sites on the body surface. The differences in electrical potential between strategically placed electrodes are recorded by electrocardiographs as voltage variations on the ordinate against time on the abscissa.

Although the electrical events in the heart can be displayed in many other ways, time-based electrocardiography is one of the most important diagnostic tools in clincal medicine. Normal and abnormal rhythms are identified and measured; the spread of electrical excitation in the heart muscle gives clues on a great number of impending, current or past pathological changes such as, e.g., localized ischemias, infarctions, necroses of tissue, etc. Recording the electrocardiogram with surface electrodes is virtually free of risk.

The interpretation of changes in the electrocardiogram waveform is the domain of expert cardiologists. Computer technology has been applied to electrocardiography with the objectives, (a), to facilitate and accelerate the evaluation of electrocardiograms in the hands of specialists as well as general practitioners, (b), to monitor the rhythm of the heart's excitation in high-risk patients automatically, (c), to transmit electrocardiograms rapidly and without distortion over the telephone to diagnostic centers and (d), to store the electrocardiograms in numerical form. All these objectives have been attained to a limited extent; rhythm abnormalities, in particular, are not detected with the help of machines that monitor the electrocardiogram continuously and can signal deviations as they occur.

The digitization of electrocardiograms for data extraction and processing is done, at the present time, by standard analog/digital conversion. This technique is nothing more than electronic curve tracing: positive and negative deviations from the isopotential line are sampled at a constant frequency and measured as discrete amplitude signals. Sampling and expressing the amplitude in discrete units carry the risk that the continuous signal waveform is not adequately represented. Any conversion error becomes visible when the digitized signal is again transformed, without further treatment, into its analog equivalent. The waveform reconstituted after A/D conversion follows the original record in steps, an averaging technique that frequently hides important information. The frequency response of non-dedicated transmission lines as well as available data storage capacities impose limitations on the sampling frequency and the number of bits representing the signal amplitude. For this reason, a number of compression methods have been devised which record only changes in the recurring signal beyond a set threshold value. It is known that these compressions can lead to serious errors.

The complex waveforms of the electrocardiogram have, to date, defied a mathematical characterization useful for the objectives mentioned above. Expressing the electrocardiogram as a Fourier series is possible but not practical for routine clinical use since a satisfactory representation in particular of the spikes in an electrocardiogram is achieved only by adding a great number of harmonics.

OBJECTS AND STATEMENT OF THE INVENTION

It is an object of the present invention to provide a method and apparatus for the mathematical characterization of a waveform using the so-called spline functions interpolation method in order to obtain a faithful reconstruction of the input waveform.

The spline function is the expression of a mathematical interpolation method which permits to lay a continuous trace through any array of points. This is accomplished in two steps: firstly, successive points are joined by usually cubic polynomials. Continuity between these separate sections on the curve is obtained by adjusting, secondly, the co-efficients in the equation for each through iteration until the tangent at the point denoting the end of one section is equal to the tangent at the same point now defining the beginning of the following one. Further detailed explanation of the spline function may be found described in an article written by B. Carnahan, H. A. Luther, J. O. Wilkes in a book entitled "Applied Numerical Methods" (John Wiley & Sons, New York, 1969).

Of particular value is the fact that the points through which the curve is traced do not have to be equidistant.

In order to arrive at a mathematical characterization of waveforms used with the present invention, the procedure in which the spline function is ordinarily employed must be modified. As will be explained further, the method of selecting the points from which a curve or waveform will then be reconstructed by the spline function must be determined. The choice of strategic points (which are called nodal points in the spline function) is crucial for the correct representation of a waveform; conversely, since only one particular sequence of points defines a given curve, their coordinates provide its complete mathematical characterization.

One notable advantage of the present method and apparatus over existing systems is that it is very precise although it requires a much smaller number of data. Also, it can be implemented at a much lower cost.

The present invention therfore relates to an apparatus for the mathematical characterization of an input waveform in order to obtain an accurate reconstruction of the waveform, the apparatus comprising:

input means detecting the waveform;

computing means operatively connected to the input means including means for selecting strategic points on the waveform and means for reconstructing a waveform from the strategic points in accordance with an interpolation method, known as spline function, whereby the reconstructed waveform characterizes the input waveform;

means connected to said computing means for displaying the reconstructed waveform.

The present invention also relates to a method for characterizing a waveform in order to obtain an accurate reconstruction of the waveform, which comprises the steps of:

selecting strategic points on the waveform;

laying a continuous trace through the points in accordance with an interpolation method known as the spline function, to form a reconstruction of said waveform; and displaying the reconstructed waveform.

Other objects and further scope of applicability of the present invention will become apparent from the detailed description given hereinafter. It should be understood, however, that this detailed description, while indicating preferred embodiments of the invention, is given by way of illustration only since various changes and modifications within the spirit and the scope of the invention will become apparent to those skilled in the art.

IN THE DRAWINGS

DESCRIPTION OF PREFERRED EMBODIMENTS

Figure 1:
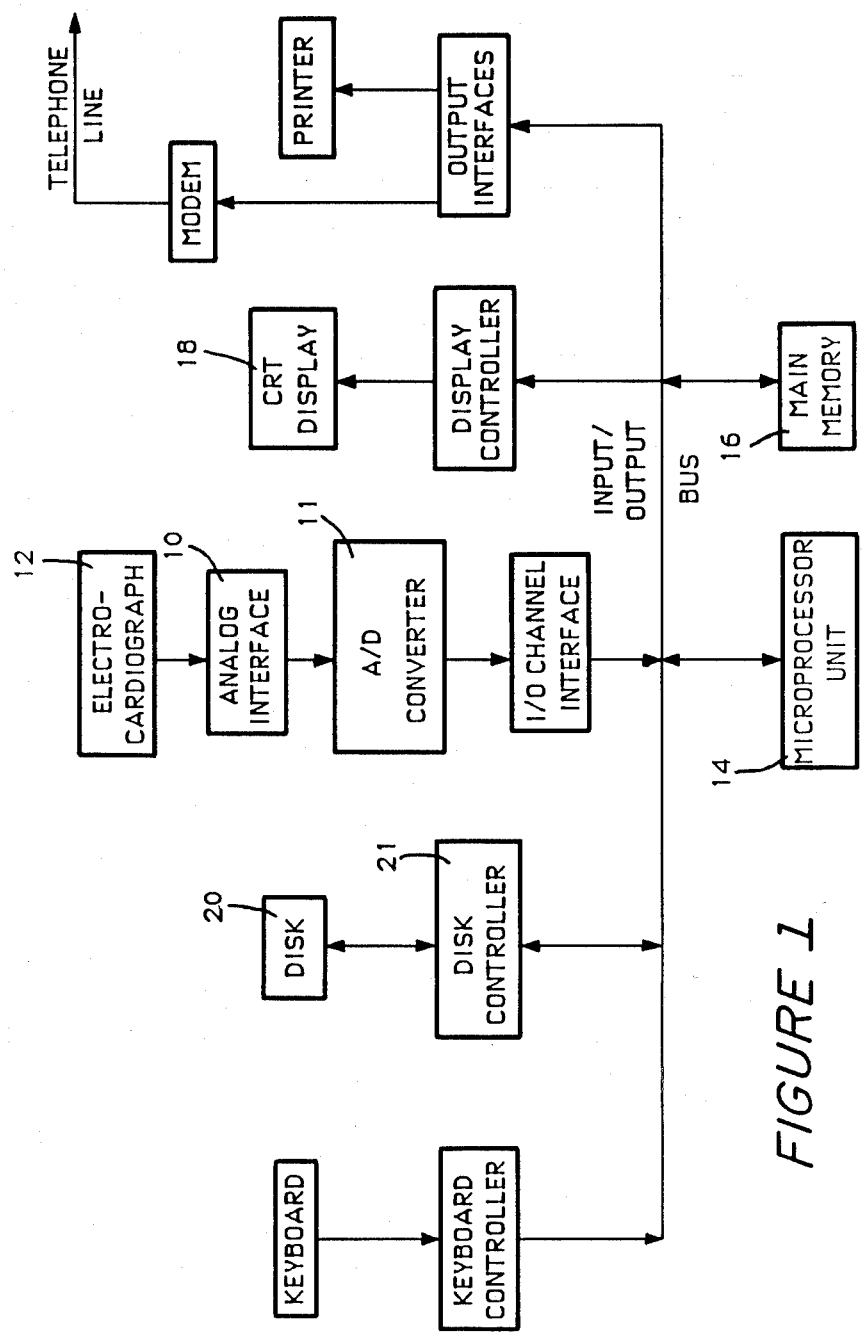
FIG. 1 is a schematic block diagram representing computing hardware and software with which the present invention can be employed.

FIG. 1 illustrates the various components which are required to construct the apparatus performing the present invention. An electronic module, consisting of an analog interface 10 and and A/D converter 11, connected to a conventional electrocardiography machine 12 converts the recorded electrical signals continuously into digital form. A microprocessor unit 14 selects from the data presented and retains only those pertinent for the characterization of each of the input waveforms. The microprocessor unit sends these data to be stored in a main memory 16 and simultaneously outputs them either in the digital form or as points superimposed on the input curve on a cathode ray tube 18. Furthermore, the microprocessor unit 14 contains the spline function program which lays a continuous trace through the nodal points. The reconstructed signal can be displayed at 18 for comparison with the original. The memory disk system 20, 21, is provided for data storage and flexible data selection, e.g. to facilitate the search for certain data profiles, to establish rating scales, etc.

Figure 2:
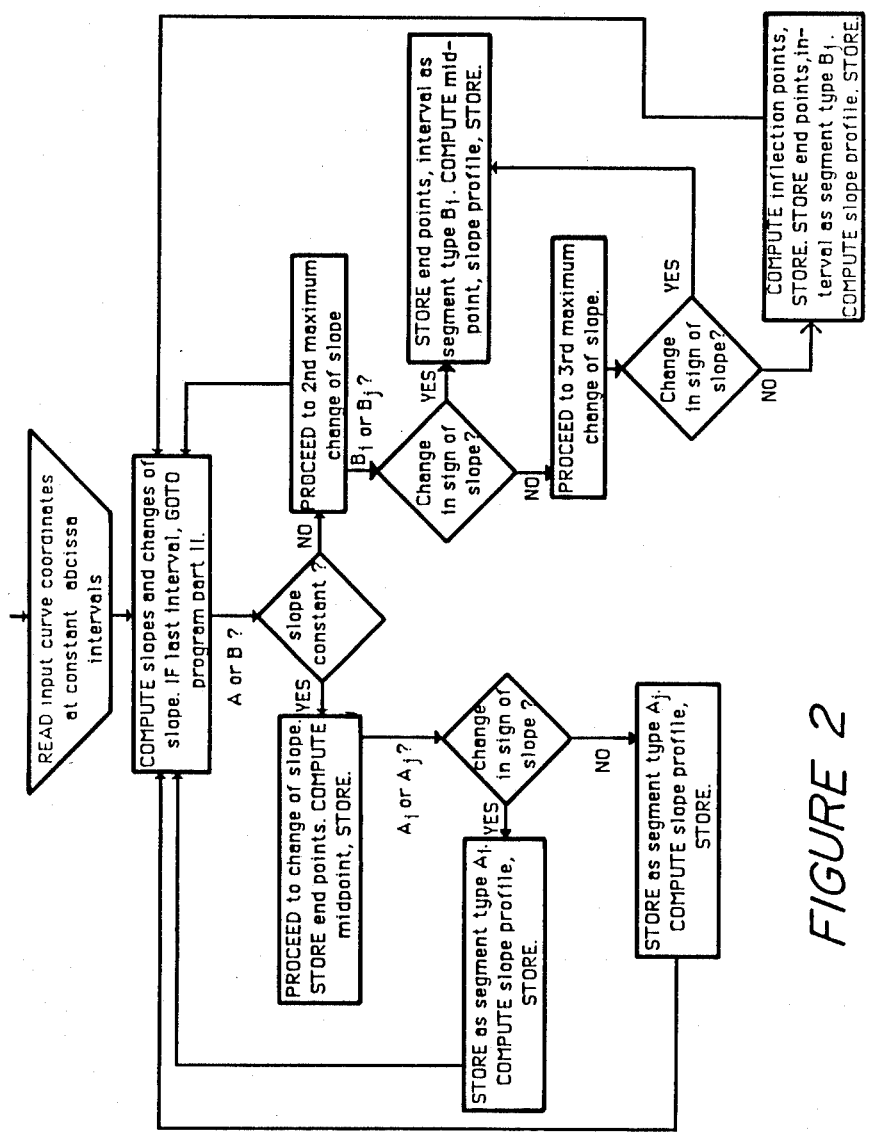
FIG. 2 is a flow chart illustrating the sequence of decisions required for the segmentation of th input curve.
Figure 3A:
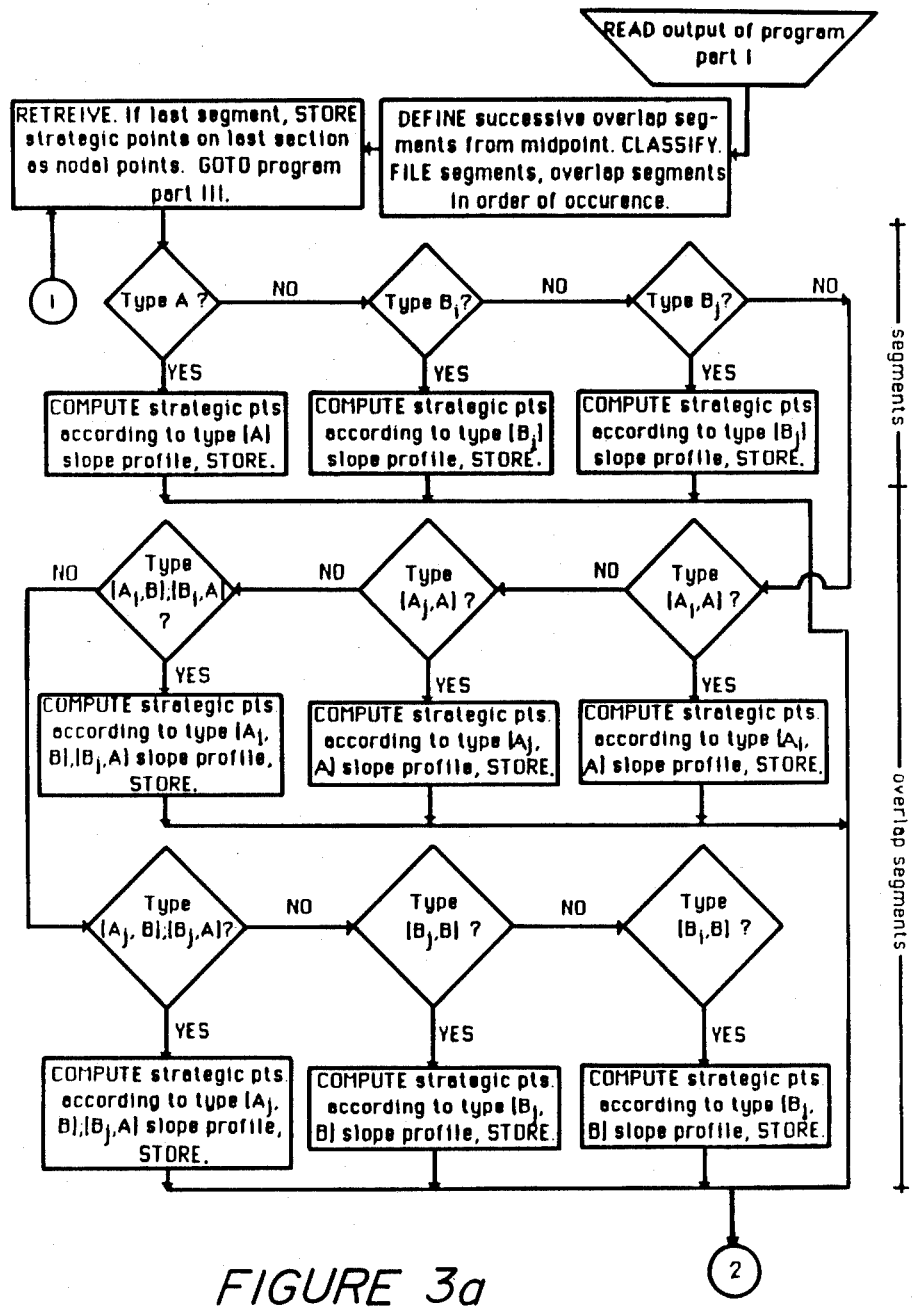
FIG. 3 is a flow chart representing the sequence of decisions required for the selection of strategic points.
Figure 3B:
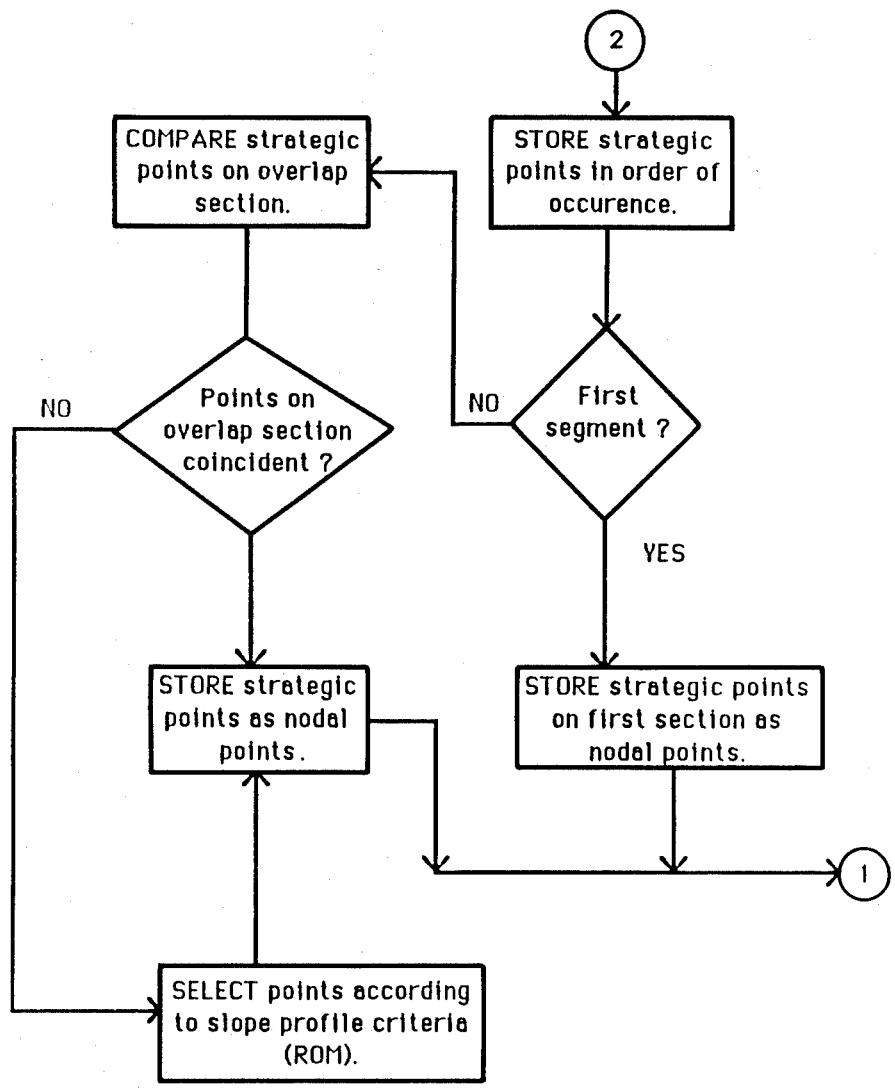

The nodal points around which the spline function reconstructs a given waveofrm are chosen in the sequence of decisions presented on flow charts of FIGS. 2 and 3. The input curve is best represented if the nodal points are spaced according to changes in slope; in general, they must be clustered tighty about abrupt changes. The first step in the process of determining where the nodal points have to lie is the definition of curve segments between specific changes of slope in accordance with the following designation:

Type designation of curve segments

Segment type $A_i$:

any straight line followed, beyond its designated end point, by a curve or another straight line with a slope of the opposite sign.

Segment type $A_j$:

any straight line followed, beyond its designated end point, by a curve or another straight line with a slope of the same sign.

Segment type $B_i$:

any curved line followed, beyond its designated end point, by a straight line or another curve with a slope of the opposite sign.

Segment type $B_j$:

any curved line followed, beyond its designated end point, by a straight line or another curve with a slope of the same sign.

In order to assure correct clustering, e.g. about the maxima of waveform spikes, the continuation of the curve has to be anticipated beyond the computed endpoint of any single segment. The selection of nodal points taking the curve's continuation into account is done in the second part of the program (FIG. 3) by defining as overlap segments, and examining, the intervals between the midpoints of successive segments. Their type classification corresponds to that of their component segments: subsegment $[A_i, A_i]$, for example, contains the overlap section of two successive segments of type $A_i$ and contains a minimum or maximum (as the case may be). The final selection of nodal points is made by comparing their location on the common section with that on its composite segments. The arguments for this comparison come from a catalog of slope profiles in the computer's read-only memory.

The slope profile is defined as a set of data typical for a segment or overlap segment and comprises, (a), the slopes at as many abscissa intervals as are necessary to characterize a curve type, and (b), the changes of slope $\Delta(\Delta y/\Delta x)$ between each set of consecutive abscissa intervals. Slope profiles are cataloged according to the following criteria, within defined limits and/or categories:

[1] pattern of specific changes of slope (e.g. flattened, S-shaped, skewed curve);
[2] total or maximum $\Delta y$ interval;
[3] total or maximum $\Delta x$ interval;
[4] chord slope ($\Delta y_{max}/\Delta x_{max}$).

The catalog of slope profiles is derived from a program that selects strategic points for various types of curves (i.e., curves defined according to specific criteria and limits). The accuracy of reconstruction of the input curve is then verified by applying the spline function program. The slope profile criteria are adjusted until all curve types are represented perfectly, i.e. with coordinate deviations from the original or less than 0.1 percent.

Some examples for the selection of strategic points according to typical slope profiles are:

(a) the flatter a waveform in the shape of a half-elipse, the further will the strategic points be located from its coordinate maximum;

(b) the position and spacing of strategic points on a straight line is a function of its length;

(c) the position and spacing of strategic points on a straight line depends directly on its slope as well as on the slope of the following segment.

Figure 4:
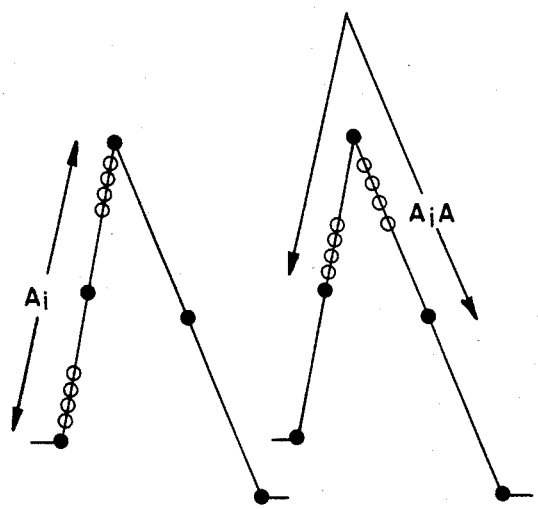
FIG. 4 is a graph for illustrating the definition of a segment and of an overlapping segment.

FIG. 4 serves to explain the purpose of the comparison process at the end of program of FIG. 3. The correct representation of the common curve section as well as the correct peak coordinates are given, in the case illustrated, by retaining as strategic points those selected from the overlap segment [$A_i$, A], in addition to the point at the curve's extreme ordinate value. The position of nodal points (empty circles) best representing the curve about its maximum is distinctly different from that for the straight line of segment $A_i$.

The strategic points retained after due comparison in the second part of the program become the nodal points of the spline function with which the reconstruction of an input waveform is accomplished. This last part of the program is written according to the flow chart given by T. N. E. Greville in 'Mathematical Methods for Digital Computers' (volume II, A. Ralston and H. S. Wilf, eds., John Wiley & Sons, New York, 1967). It is not reproduced here since it is part of the current mathematical literature and readily available.

The interpolation method presented is not merely useful for reproducing or simulating an input curve but also characterizes it mathematically: the set of nodal points selected is unique for a given curve and only one characteristic value for its definite integral is obtained. Changes in a waveform can thus be recorded by shifts in the location of nodal points. Since the completed program yields the coordinates of the nodal points as well as the 1st and the 2nd derivatives at these points, the explicit equation for a curve can be written, if desired (see ref. Greville, cited above).

Any electrocardiographic trace can be characterized mathematically by the method given here. It should be clear from the description that the location of nodal points on the curve is crucial for its correct representation. The microcomputer implementing the present method will therefore first perform the task of selecting nodal points according to the program parts illustrated in FIGS. 2 and 3 and will then use these points for the reconstruction of the original curve by spline interpolation.

Figure 5:
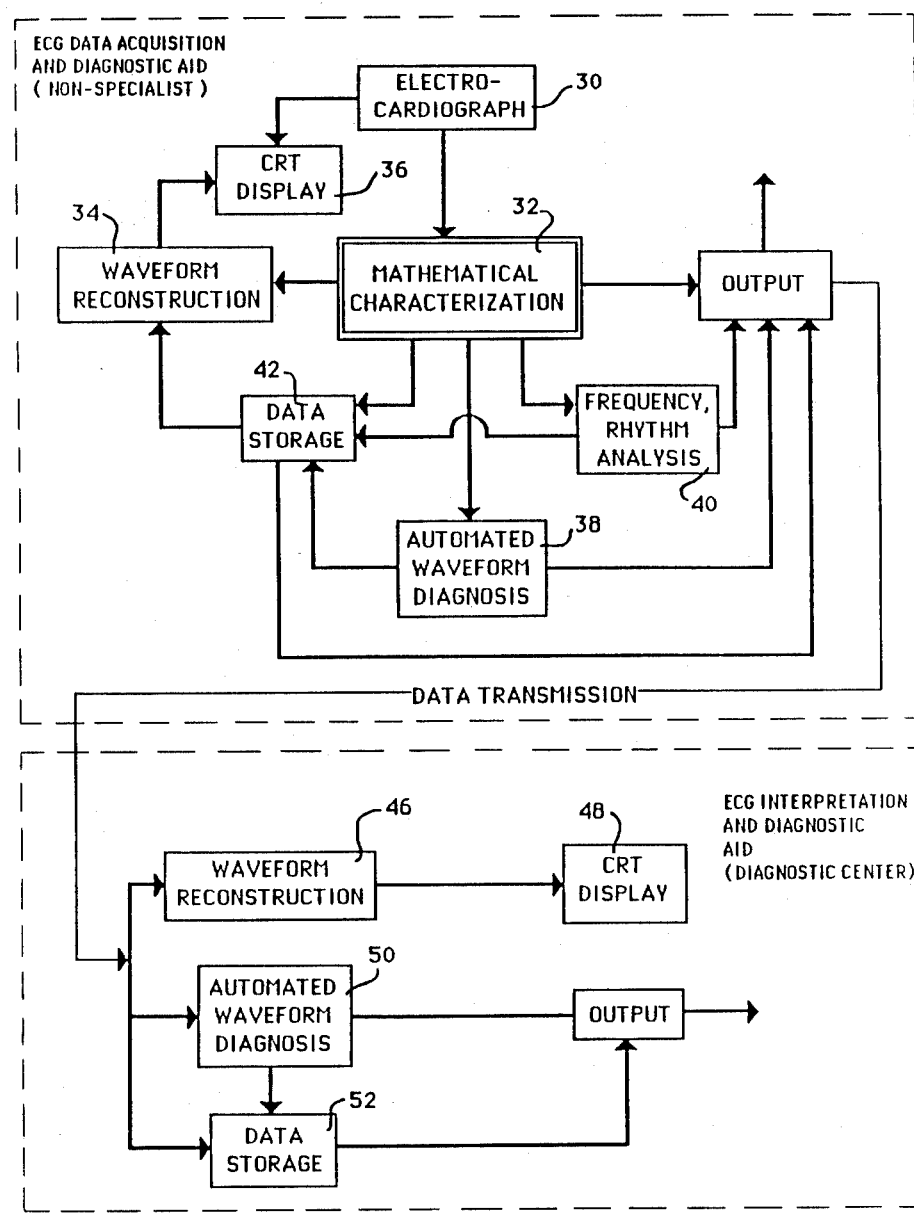
FIG. 5 is a block diagram providing a complete system of electrocardiogram data acquisition, interpretation and analysis based on the method of the present invention with the option of data transmission to a remote diagnostic center.

The advantages of the present method of characterizing electrocardiographic records mathematically are best realized with reference to FIG. 5. There is shown, on the left, a microcomputer system capable of performing automatically the functions described, attached to an electrocardiograph 30. At a location remote from this data acquisition center is (shown on the right) a microcomputer at a diagnostic center, corresponding through a telephone line with the former. The core of the system described is the mathematical characterization module 32 from which the original waveform is reconstructed at 34 and displayed at 36, for comparison with the original. The same system also provides an automated waveform diagnosis at 38 by referring to a bank or catalog of nornal and pathological waveforms, all expressed by their respective sets of nodal points required for a precise reconstruction with the help of the spline function. An analysis of frequency and rhythm of the heart beat is done at 40 by identifying certain characteristic features of each electrical signal (such as the maximum of the wave in the electrocardiogram), measuring their absolute and relative occurences on a time scale and comparing the results, again, with a bank of data in which normal and pathological profiles are filed for reference. Apart from the display, at least two output formats should be available to give the data in print and to transmit them directly via telephone modem. The output data can also be stored at 42 and recalled when needed, e.g. to establish a patient's history, or, for research purposes.

To the right of the dashed line is a diagnostic center which further analyzes and interprets the transmitted electrocardiogram data. The nodal points can again be used for reconstructing at 46 the original waveform to be displayed on a cathode ray tube 48. The automated waveform diagnosis module 50 operates in the same way and with reference to a data storage unit 52 identical to that at the point of data acquisition. It has the purpose of confirming the computer diagnosis as well as fulfilling the tedious task of measuring amplitudes and durations. The cardiologist at the diagnostic center who receives an electrocardiogram from a remote location will, with the minimal system demonstrated, be able to reconstruct the original waveform by applying the spline interpolation program to the nodal points sent to him. He will also have access to, and control over, all results of the automated diagnostic aid.

The system could, of course, be made completely symmetrical about the dashed line in FIG. 5, to reproduce the apparatus at the point of acquisition also at the diagnostic center.

The system as described presents numerous advantages over existing methods used to express electrocardiograms in numerical form. The spline interpolation needs only a relatively small but carefully selected number of points on a curve to reconstruct the original. It is not a requirement that the points be equidistant. The nodal points are found automatically by the computer. If they were not chosen correctly, the reconstructed waveform will differ from the original (a convenient visual check) and this is the reason why, conversely, the set of nodal points fully characterizes the input waveform. Thus, it will be sufficient to list the coordinates of the particular set of nodal points and their variation as indicators for changes occuring in the electrocardiogram.

Even the most complex electrocardiograms can be reconstructed by the present invention with invariably fewer than 120 points per beat. This is only one third the number of points required by the American Heart Association as standard for A/D conversion. The present method can be pushed to reproduce every jitter of noise in the original waveform. This level of precision is achieved with a quantity of data small enough to be sent easily over ordinary (1 nondedicated') telephone lines, without risk of distortion. Finally, the apparatus implementing the present method uses available technology and will easily interface with existing electrocardiographs as well as conventional microcomputers and their associated equipment for output and transmission.

Although the invention has been described above with respect to one specific form, it will be evident to persons skilled in the art that it may be refined and modified in various ways. It is therefore wished to have it understood that the present invention should not be limited in interpretation except by the terms of the following claims.

The embodiments of the invention in which an exclusive property or privilege is claimed are defined as follows:

1. An apparatus for mathematically characterizing an input electrocardiographic waveform for obtaining a reconstruction of said input electrocardiographic waveform, said apparatus comprising:

input means for detecting said input electrocardiographic waveform;

computing means operatively connected to said input means for performing the steps of:

segmentalizing said input waveform into main segments and establishing a midpoint for each main segment;

defining overlapping segments of said main segments, each overlapping segment extending between midpoints of two successive main segments and defining a common section with a corresponding main segment;

selecting main strategic points for each main segment and overlapping strategic points for each overlapping segment;

generating a set of characteristic data for each common section by comparing said main strategic points with said overlapping strategic points over corresponding common sections; and producing a reconstructed electrocardiographic waveform corresponding to said input waveform from said selected main and overlapping strategic points in accordance with an interpolation method using a spline function, whereby the reconstructed waveform mathematically characterizes the input electrocardiographic waveform; and means for displaying said reconstructed waveform.

2. An apparatus as defined in claim 1, wherein said first means segmentalizes said input waveform in main segments by determining portions of said input waveform, each of said portions responding to predetermined criteria and being defined as main segments.

3. An apparatus as defined in claim 2, wherein said predetermined criteria are:

(a) whether each of said portions has a constant slope or a variable slope;

(b) whether an immediately following portion has a constant slope or a variable slope; and (c) the sign of the slope of said immediately following portion.

4. An apparatus as defined in claim 1, wherein said input means comprises an analogdigital convertor for digitalizing said waveform.

5. An apparatus as defined in claim 1, further comprising means for transmitting said strategic points at a point remote from said input means, said input waveform being reconstructed at said remote point.

6. An apparatus as defined in claim 1, further comprising means for determining the frequency of said input electrocardiographic waveform and the regularity of its component peaks and waves.

7. A method for mathematically characterizing an input electrocardiographic waveform for obtaining a reconstruction of said input electrocardiographic waveform, said method comprising the steps of:

segmentalizing said input waveform into main segments;

establishing a midpoint for each main segment;

defining overlapping segments of said main segments, each overlapping segment extending between midpoints of two successive main segments and defining a common section with a corresponding main segment;

selecting main strategic points for each main segment and overlapping strategic points for each overlapping segment;

generating a set of characteristic data for each common section by comparing said main strategic points with said overlapping strategic points over corresponding common sections;

laying a continuous trace through the selected main and overlapping strategic points in accordance with an interpolating method using a spline function so as to form a reconstructed electrocardiographic waveform corresponding to said input electrocardiographic waveform; and displaying the reconstructed electrocardiographic waveform.

8. A method for mathematically characterizing an input electrocardiographic waveform, said method comprising the steps of:

converting into digital form said input electrocardiographic waveform;

segmentalizing said digitized input waveform into main segments;

establishing a midpoint for each main segment;

defining overlapping segments of said main segments, each overlapping segment extending between midpoints of two successive main segments and defining a common section with a corresponding main segment;

selecting main strategic points for each main segment and overlapping strategic points for each overlapping segment;

generating a set of characteristic data for each common section by comparing said main strategic points with said overlapping strategic points over corresponding common sections;

laying a continuous trace through said selected main and overlapping strategic points in accordance with an interpolation method using a spline function to thereby form a reconstructed electrocardiographic waveform corresponding to said input electrocardiographic waveform; and displaying said reconstructed electrocardiographic waveform.

* * * * *